United States Patent
Van Der Brug et al.

[11] Patent Number: 6,112,113
[45] Date of Patent: Aug. 29, 2000

[54] IMAGE-GUIDED SURGERY SYSTEM

[75] Inventors: Willem P. Van Der Brug; Paulus M. C. Gieles; Adrianus J. E. M. Dankers; Jacobus G. M. Van Den Goor, all of Eindhoven, Netherlands

[73] Assignee: U.S. Philips Corporation, New York, N.Y.

[21] Appl. No.: 09/109,872

[22] Filed: Jul. 2, 1998

[30] Foreign Application Priority Data

Jul. 3, 1997 [EP] European Pat. Off. .............. 97202044

[51] Int. Cl.[7] ....................................... A61B 5/05
[52] U.S. Cl. ........................................ 600/427; 606/130
[58] Field of Search .................... 600/407, 414, 600/415, 417, 424, 426, 429, 427; 606/130

[56] References Cited

U.S. PATENT DOCUMENTS

| | | | |
|---|---|---|---|
| 5,309,101 | 5/1994 | Kim et al. ................................. | 324/309 |
| 5,389,101 | 2/1995 | Heilbrun et al. ......................... | 606/130 |
| 5,617,857 | 4/1997 | Chader et al. ......................... | 138/653.1 |
| 5,695,501 | 12/1997 | Carol et al. ............................. | 606/130 |
| 5,797,924 | 8/1998 | Schulte et al. .......................... | 606/130 |
| 5,891,157 | 4/1999 | Day et al. ............................... | 606/130 |
| 5,921,992 | 7/1999 | Costales et al. ........................ | 606/130 |

FOREIGN PATENT DOCUMENTS

WO9611624 4/1996 WIPO .
WO9729678 8/1997 WIPO .

*Primary Examiner*—Brian L. Casler
*Attorney, Agent, or Firm*—Dwight H. Renfrew

[57] ABSTRACT

An image-guided surgery system includes a position measuring system (9, 10) for measuring a position of an instrument (20). The image-guided surgery system includes a test system (9, 10, 30) which is arranged to measure the instrument, using the position measuring system, by measuring a calibration position of a reference part (42) of the instrument while an object part (23) of the instrument is situated in a calibration location. The test system is also arranged to measure a test position of the reference part of the instrument while the object part of the instrument is situated in a test position.

10 Claims, 2 Drawing Sheets

IMAGE-GUIDED SURGERY SYSTEM

BACKGROUND OF THE INVENTION

1. Field of the Invention
2. Description of Related Art Image-guided surgery system The invention relates to an image-guided surgery system which includes a position measuring system for measuring a position of an instrument.

An image-guided surgery system of this kind is known from the U.S. Pat. No. 5,389,101.

An image-guided surgery system is used to display a position of a surgical instrument in an operating zone within the body of a patient to a user, for example a surgeon, during a surgical intervention. Images of the patient, for example CT or MR images, are formed prior to the operation. The image-guided surgery system includes a position measuring system for measuring the position of the surgical instrument. The image-guided surgery system also includes a computer for deriving corresponding positions in a relevant image from the measured positions of the surgical instrument. During the operation the position measuring system measures the position of the surgical instrument relative to the patient and the computer calculates the position in such a previously formed image which corresponds to the measured position of the surgical instrument. A monitor displays the previously formed image in which the actual position of the surgical instrument is reproduced. The image on the monitor shows the surgeon exactly where in the operating zone the surgical instrument is located, without the surgeon having a direct view of the instrument. The image displayed on the monitor thus shows the surgeon how to move the surgical instrument in the operating zone without high risk of damaging of tissue and notably without risk of damaging of vital organs.

An image-guided surgery system of this kind is used, for example in neurosurgery in order to show the surgeon exactly where the surgical instrument is located in the brain during cerebral surgery.

The known image-guided surgery system can be used only if the dimensions of the instrument are accurately known already. The instrument is provided with light-emitting diodes (LEDs) which emit light which is detected by the position measuring system so as to measure the position of the LEDs. The position of the LEDs on the instrument, relative to an end of the instrument, must be constant and accurately known so as to enable the position of the end of the instrument to be accurately derived from the measured positions of the LEDs on the instrument.

SUMMARY OF THE INVENTION

It is an object of the invention to provide an image-guided surgery system which enables easy, fast and accurate measurement of the instrument.

This object is achieved by means of an image-guided surgery system according to the invention which is characterized in that the image-guided surgery system includes a test system for measuring the instrument, using the site measuring system, by measuring a calibration site of a reference part of the instrument while an object part of the instrument is situated in a calibration site, and by measuring a test site of the reference part of the instrument while the object part of the instrument is situated in a test site.

The test system measures the instrument in such a manner that the relevant distances within the instrument become accurately known. The test system notably measures the distance and the direction of the reference part relative to the object part. By performing two measurements, i.e. one with the object part in the calibration site and one with the object part in the test site, measurement of the instrument is reliably and accurately performed. The occurrence of a significant difference between the results of the two measurements forms an indication that an error has been made during one of the measurements. The test system detects notably whether such an error occurs because the object part has been placed in the calibration site without due care, since it is practically impossible to position the object part in the test site in an equally careless manner.

The reference part is notably a part of the instrument whose site is measured by the site measuring system. For example, the reference part includes a transmitter unit which transmits a signal which represents the site of the reference part and is detected by the site measuring system. For example, the transmitter unit includes LEDs or IREDs and the site measuring system includes CCD image sensors which are sensitive to light or infrared radiation. Furthermore, the object part of the instrument is notably a part which is functional during the execution of a medical diagnostic or therapeutic treatment. For example, the object part is a tip of a biopsy needle, the beak of a pair of pliers or an objective lens of an endoscope.

The site measuring system measures the site of the reference part during the operation. Because the distance and the direction of the object part relative to the reference part have also been measured, the site of the object part can be derived from the measured site of the reference part during the operation. In a previously formed image of the anatomy of the patient the site of the object part is reproduced inter alia on the basis of the derived site of the object part.

Because sites of the calibration site and/or the test site are measured by means of the position measuring system, it is achieved that the calibration site and the test site can be chosen arbitrarily as is best suitable for the relevant operation. The calibration and test sites are preferably chosen so that the measurement of the instrument is not disturbed by a variety of other equipment required for the operation. The distance and the direction of the object part relative to the reference part are derived from the positions of the calibration site, the test site and the reference position, measured by means of the position measuring system. When the calibration site and the test site essentially coincide, only little time will be required to measure the instrument. This is because little time is lost, notably because the object part need not be displaced over a long distance from the calibration site to the test position. Furthermore, if these positions accurately coincide, only one measurement of the positions of the calibration site and the test site is required. Moreover, it is possible to use a single module in which the instrument is arranged with the object part in the calibration site and the test site for both measurements. When such a single module is used, it is handy to measure the position of the calibration and test sites by measuring the position of the module by means of the position measuring system. It is notably attractive to provide the module with a transmitter unit, for example in the form of LEDs or IREDs which emit a signal representing the position of the module and hence of the calibration and test positions.

When it is ensured that the orientation of the object part in the calibration location, relative to the reference part, differs from the orientation of the object part in the test location, relative to the reference part, it is practically impossible for an error to remain unnoticed. When the object part is not carefully arranged in the calibration site, it is practically impossible to arrange the object part in the test site in an equally careless manner so that the test system does not detect any difference between the results of the measurements of the calibration site and the test site of the reference part. It is notably practically impossible that an error remains unnoticed during the measurement of the calibration position.

The reference part of the instrument is preferably provided with a transmitter unit. The position measuring system measures the position of the reference part by detecting the position signal from the transmitter unit. The test system derives the distance and the direction of the object part, relative to the reference part, on the basis of the position of the reference part, and the calibration site or the test site. Performing two measurements, i.e. once with the object part in the calibration site and once with the object part in the test position, makes the result of the measurements very reliable and accurate. Because the distance from and the direction of the object part relative to the reference part are particularly accurately and reliably measured, it is not necessary to mount the transmitter unit on the reference part in an accurate and reproducible manner. It is notably possible to use a detachable transmitter unit. Consequently, a variety of instruments can be used in conjunction with the image-guided surgery system without it being necessary for these instruments to be specially designed. It is notably not necessary to design instruments specifically so as to be provided with a transmitter unit; it is much easier to use a detachable transmitter unit as desired and to attach such a detachable transmitter unit temporarily to the relevant instrument during the operation. The part of the instrument carrying the transmitter unit then acts as the reference part.

The difference between the results of the measurement of the calibration position and the test position represents the measuring accuracy of the position measuring system if the object part has been carefully arranged in the calibration site and in the test site. The precision of the position measuring system can thus be derived from the difference between the results of the two measurements. This precision represents important information to the user in order to ensure that during the operation the instrument, notably the object part, reaches a desired position, utilizing the previously formed images in which the current position of the instrument within the body of the patient is reproduced.

On the basis of the differences between the measures provided by the two measurements, the user can decide whether the measurement of the instrument is sufficiently accurate.

BRIEF DESCRIPTION OF THE DRAWINGS

These and other aspects of the invention will be described in detail hereinafter with reference to the following embodiments and the accompanying drawing; therein.

DESCRIPTION OF THE PREFERRED EMBODIMENTS

Figure 1:
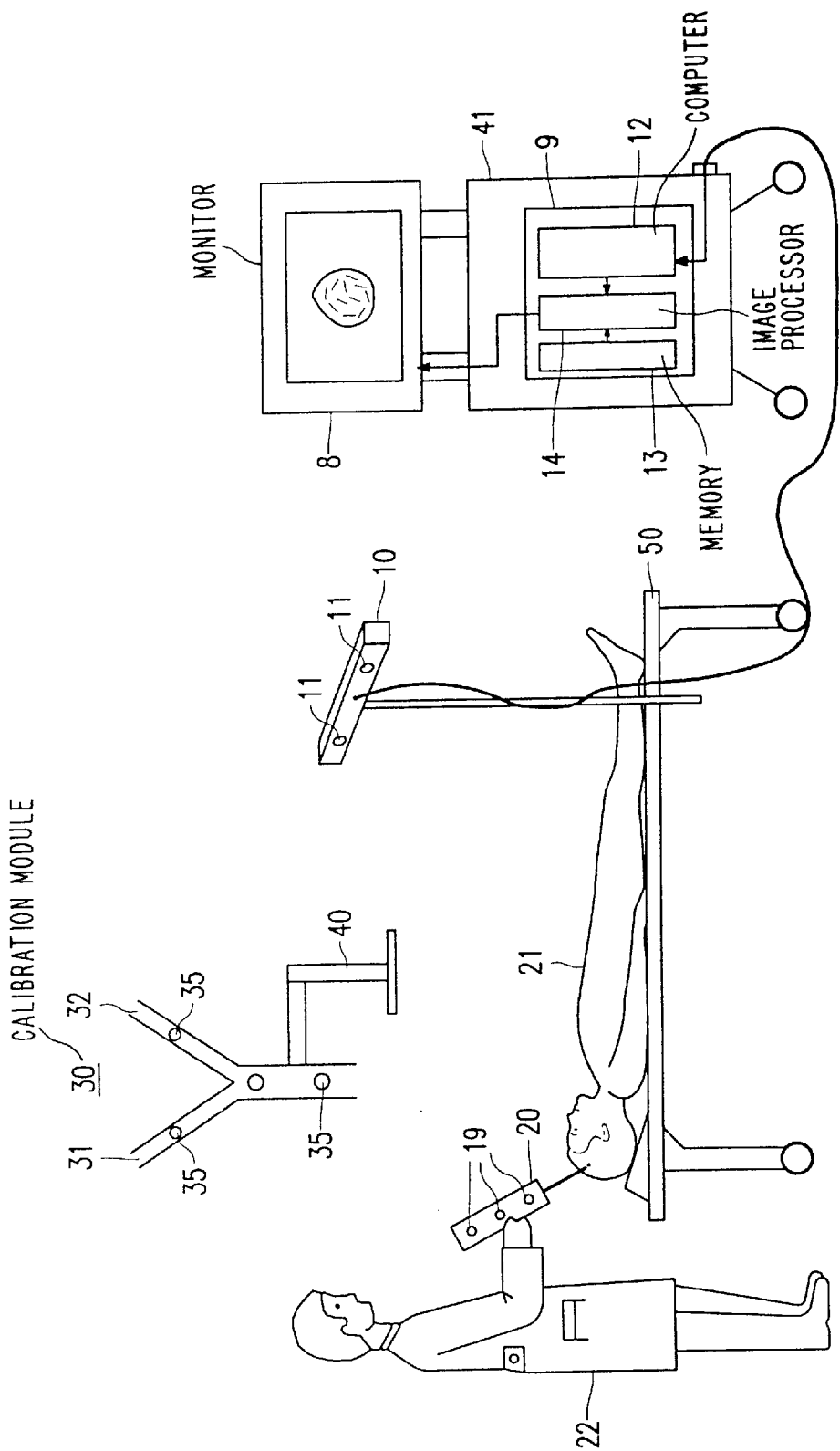
FIG. 1 shows diagrammatically an image-guided surgery system according to the invention.

FIG. 1 is a diagrammatic representation of an image-guided surgery system according to the invention. The image-guided surgery system includes a position measuring system with a camera unit 10 and two CCD image sensors 11. The camera unit 10 is attached to a patient table 50. The camera unit 10 forms images of the surgical instrument 20 from different directions. The surgical instrument is provided with a plurality of, for example three infrared emitting diodes (IREDs) 19. The CCD image sensors supply image signals, notably electronic video signals, which represent the individual images of the instrument 20, notably of the IREDs 19. The position measuring system also includes a computer 12 for deriving the position of the instrument from the image signals. Image information of the patient 21 to be examined or treated is stored in an image memory 13. This image information concerns, for example MRI and/or CT images formed before or during the surgical treatment. Marks on or in the patient 21 are also reproduced in the images of the patient. The position measuring system measures the positions of the marks, for example by pointing out the marks by means of the instrument. The computer 12 derives the relation between positions in or on the patient 21 and the corresponding positions in the images from the positions of the marks and the positions of the reproductions of the marks in the images formed. On the basis of the measured position of the instrument 20 and said relation, the image processor 14 forms an image signal which represents an image which shows image information of the patient 21 in which the current position of the instrument 20 within the patient is reproduced. The computer 12, the image memory 13 and the image processor are included in a data processor 9 whereto a monitor 8 is connected. The image signal is applied to the monitor 8. The monitor 8 shows image information of the patient 21 in which the position of the surgical instrument 20 is reproduced. The user 22, for example the surgeon or an assistant, can thus move the surgical instrument 20 within the patient 21 without having a direct view thereof and without risk of unnecessary damaging of tissue.

Figure 2:
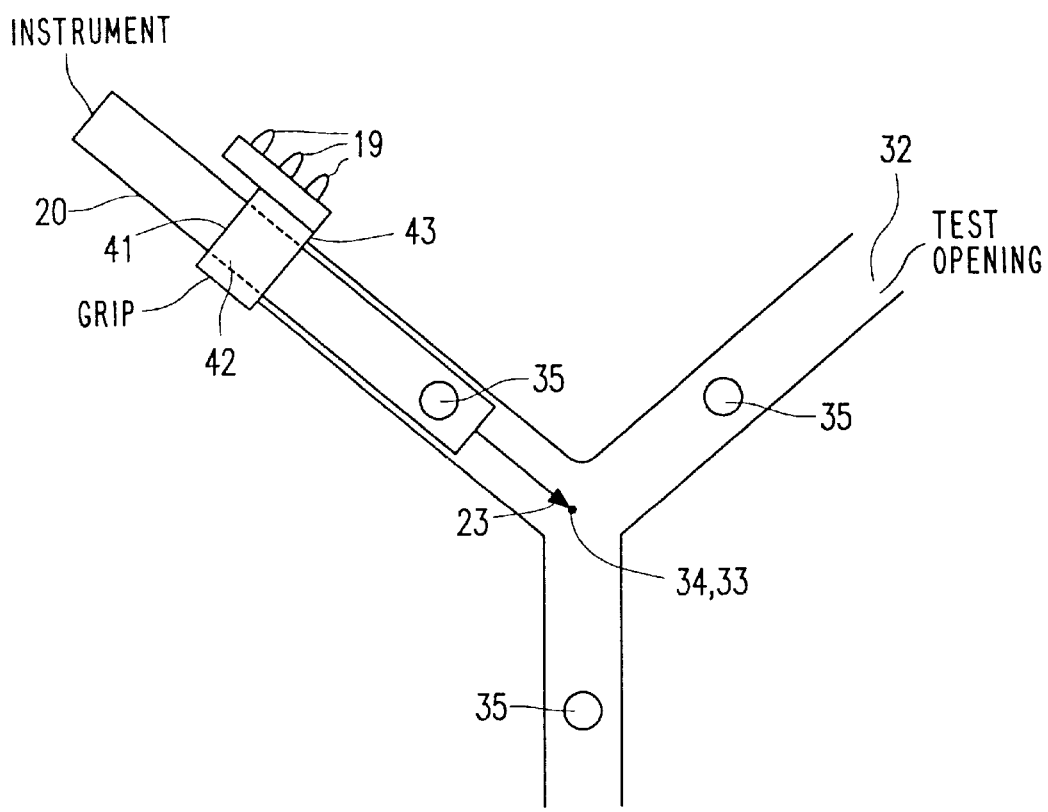
FIG. 2 shows a detail of a module in which the calibration and test positions are included.

With reference also to FIG. 2, in order to ensure that the position of the end 23 of the instrument 20 can be accurately calculated from the position of the LEDs or IREDs 19 on the instrument 20, the instrument 20 itself is measured. The instrument is, for example a biopsy needle having a grip 42 and a sharp end 23. The instrument 20 is arranged in a module 30 in order to carry out a calibration measurement. The module 30 is suitably arranged within the operating room, within reach of the camera unit 10. The module 30 is mounted, for example on a separate stand 40 or on the housing 41 accommodating the data processor 9. The module comprises two openings, i.e. a calibration opening 31 and a test opening 32. When the instrument 20 is inserted into one of the openings, the end 23 of the instrument 20 is positioned in the calibration position 33 or the test position 34. The module 30 includes a transmitter unit, for example LEDs or IREDs 35, like those of the instrument 20. When the instrument 20 has been arranged in the calibration opening 31, so that its end occupies the calibration position, the camera unit detects the position of the LEDs or IREDs 19 on the instrument and the position of the LEDs or IREDs 35 of the module. The cameras 11 apply calibration signals, representing positions of the LEDs or IREDs 19 and 35, to the computer 12. Such calibration signals are, for example electronic video signals. The computer 12 calculates the positions of the module and the instrument relative to one another on the basis of the signal levels of the calibration signals from the camera unit 10, and derives the positions of the end 23 of the instrument 20 relative to the LEDs or IREDs 19 of the instrument therefrom. Subsequently, in order to execute a test measurement the instrument 20 is arranged in the test opening 32 so that its end 23 is situated in the test site. The camera unit 10 again detects the positions of the LEDs or IREDs 19, 35 of the instrument 20 and of the module 30, respectively. The cameras 11 supply the computer 12 with test signals representing the positions of the LEDs or IREDs 19, 35. Such test signals are, for example electronic video signals. The computer calculates the positions of the module 30 and the instrument relative to one another from the signal levels of the test signals and derives the positions of the end 23 of the instrument 20 relative to the LEDs or IREDs 19 of the instrument therefrom. Furthermore, the computer 12 compares the results of the calibration measurement and the test measurement. This difference is reproduced, for example on the monitor 8, in order to allow the user to enable the image-guided surgery system and/or to determine the accuracy of the image-guided surgery system. It is particularly advantageous to construct the module 30 so as to be portable so that the user can hold the module in the hand so as to insert the instrument therein for measurement. Such a portable module is very suitable for quickly measuring an instrument; moreover, during the measurement of the instrument the user will not be bothered by other equipment present in the operating room.

FIG. 2 shows a detail of a module in which the calibration and test positions are included. The calibration opening 31 and the test opening 32 are formed in such a manner that when the instrument 20 is inserted into the relevant openings until it abuts against an abutment 43, the end 23 of the instrument 20 will be in the calibration site or the test site. The calibration site and the test site are situated in the same location in the module shown in the example, and the orientations of the instrument 20 in the calibration site and the test site enclose an angle of approximately 90° relative to one another. The functions of the test system are performed by the position measuring system with the computer 9 and the module 30.

The LEDs or IREDs constituting the transmitter unit of the instrument are detachably mounted on the grip 42 of the instrument 20, for example by means of an elastic clamp 41. The grip 42 acts as the reference part and the end 23 is an example of the object part. Such a transmitter unit can be readily exchanged between different instruments without their own, fixed transmitter units.

All references cited herein, as well as the priority document European Patent Application 97202044.0 filed Jul. 3, 1997, are incorporated herein by reference in their entirety and for all purposes to the same extent as if each individual publication or patent or patent application was specifically and individually indicated to be incorporated by reference in its entirety for all purposes.

What is claimed is:

1. A surgical instrument measurement system for use in an image-guided surgery system comprising:
    a position measuring system for measuring positions, and
    a test system for measuring a surgical instrument having a reference part an and object part, wherein the test system comprises
        a calibration site having a determined calibration position, wherein the instrument assumes a calibration position when the object part of the instrument is situated at the calibration site,
        a test site having a determined test position, wherein the instrument assumes a test position when the object part of the instrument is situated at the test site, wherein the calibration position of the instrument differs from the test position of the instrument, and
        means for calculating the relative measurements of the object part of the instrument with respect to the reference part of the instrument from the determined calibration position of the calibrations site and the determined test position of the test site and measurements by the position measuring system of the calibration position of the reference part of the instrument while the object part of the instrument is situated in the calibration site of the test system, and of the test position of the reference part of the instrument while the object part of the instrument is situated in the test site of the test system.

2. The system as claimed in claim 1, wherein the calibration position of the calibration site and the test position of the test site are determined by means of the position measuring system.

3. The system as claimed in claim 1 wherein the position of the object part of the instrument when situated at the calibration site and the position of the object part of the instrument when situated at the test site essentially coincide.

4. The system as claimed in claim wherein the calibration site and the test site are configured so that the orientation of the object part and the reference part while the object part is situated in the calibration site is substantially perpendicular to the orientation of the object part and the reference part while the object part is situated in the test site.

5. The system as claimed in claim 1 wherein the position measuring system is responsive to position signals, and wherein the reference part of the instrument is provided with a transmitter unit for transmitting position signals which represent the position of the reference part.

6. The system as claimed in claim 5 wherein the transmitter unit is detachably connected to the reference part.

7. The system as claimed in claim 1 wherein the means for calculating is further for deriving an accuracy of the measurement of the instrument on the basis of the measured calibration position and the measured test position.

8. The system as claimed in claim 7 wherein the means for calculating is further for deriving respective relative measurements of the instrument from the measurements in the calibration position and the measurements in the test position, and and wherein the system further comprises means for reproducing a difference between the respective relative measurements.

9. The system of claim 1 further comprising a module having a calibration opening for accepting the instrument in order to situate the object part of the instrument at the calibration site, and a test opening for accepting the instrument in order to situate the object part of the instrument at the test site.

10. A method of measuring a surgical instrument for use in association with image-guided surgery system, the method comprising:
    situating an object part of a surgical instrument at a calibration site having a determined calibration position, wherein the instrument assumes a calibration position when the object part of the instrument is situated at the calibration site,
    measuring the calibration position of a reference part of the instrument while the object part of the instrument is situated in the calibration site by means of a position measuring system capable of measuring positions,
    situating the object part of the instrument at a test site having a determined test position, wherein the instrument assumes a test position when the object part of the instrument is situated at the test site, wherein the calibration position of the instrument differs from the test position of the instrument,
    measuring the test position of the reference part of the instrument while the object part of the instrument is situated in the test site by means of the position measuring system, and
    calculating the relative measurements of the object part of the instrument with respect to the reference part of the instrument from the determined calibration position of the calibration site and the determined test position of the test site and from the measurements of the instrument made when the instrument is situated at the calibration site and at the test site.

* * * * *